(12) United States Patent
Vishwakarma et al.

(10) Patent No.: US 11,086,473 B2
(45) Date of Patent: Aug. 10, 2021

(54) SYSTEM AND METHOD FOR AIDING COMMUNICATION

(71) Applicant: Tata Consultancy Services Limited, Mumbai (IN)

(72) Inventors: Arpit Vishwakarma, Kolkata (IN); Aniruddha Sinha, Kolkata (IN); Ratnamala Manna, Pune (IN); Debatri Chatterjee, Kolkata (IN); Vedraj, Pune (IN); Kingshuk Chakravarty, Kolkata (IN); Rajat Kumar Das, Kolkata (IN); Anagha Nikhil Mehrotra, Kolkata (IN); Arpan Pal, Kolkata (IN); Rahul Dasharath Gavas, Kolkata (IN); Anwesha Khasnobish, Kolkata (IN); Abhijit Das, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 0 days.

(21) Appl. No.: 16/321,286

(22) PCT Filed: May 23, 2017

(86) PCT No.: PCT/IB2017/053017
§ 371 (c)(1),
(2) Date: Jan. 28, 2019

(87) PCT Pub. No.: WO2018/020334
PCT Pub. Date: Feb. 1, 2018

(65) Prior Publication Data
US 2019/0171348 A1    Jun. 6, 2019

(30) Foreign Application Priority Data
Jul. 28, 2016  (IN) .............................. 201621025832

(51) Int. Cl.
*A61B 5/11* (2006.01)
*A61B 5/369* (2021.01)
(Continued)

(52) U.S. Cl.
CPC ........ *G06F 3/04815* (2013.01); *A61B 5/1114* (2013.01); *A61B 5/369* (2021.01);
(Continued)

(58) Field of Classification Search
USPC ....................................................... 715/850
See application file for complete search history.

(56) References Cited

U.S. PATENT DOCUMENTS 5,956,667 A * 9/1999 Higginbotham ........ G06F 17/21
340/4.1
7,747,325 B2 * 6/2010 Dilorenzo ............ A61N 1/3605
607/45
(Continued)

FOREIGN PATENT DOCUMENTS

WO    WO-2015/066332    5/2015

OTHER PUBLICATIONS

Rajan, D. et al. "Health Monitoring Laboratories by Interfacing Physiological Sensors to Mobile Android Devices," *2013 IEEE Frontiers in Education Conference (FIE)*, Oct. 23-26, 2013, Oklahoma City, Oklahoma, US; pp. 1-7.
(Continued)

*Primary Examiner* — Henry Orr
(74) *Attorney, Agent, or Firm* — Finnegan, Henderson, Farabow, Garrett & Dunner LLP

(57) ABSTRACT

System and method for aiding communication for subjects suffering from paralysis of muscles controlled by peripheral nervous system are disclosed. A method for aiding communication for said subjects includes capturing, from a plurality of sensors, sensor data generated based on an interaction of
(Continued)

a subject with an interactive UI. The plurality of sensors includes one or more body-parts movement tracking sensors for tracking motion of body-parts of the subject and one or more physiological signal sensors for monitoring physiological signals generated from the subject during the interaction. A plurality of model parameters indicative of characteristics of the subject related to the interaction are determined based on the sensor data. The navigation at the interactive UI is controlled on the plurality of model parameters.

18 Claims, 8 Drawing Sheets

(51) Int. Cl.
 *G02B 27/00* (2006.01)
 *A61B 5/398* (2021.01)
 *G06F 3/0481* (2013.01)
 *G06F 3/01* (2006.01)
 *G06F 3/00* (2006.01)
 *A61F 4/00* (2006.01)
 *H04N 7/18* (2006.01)
 *G09B 5/06* (2006.01)
 *G06N 20/00* (2019.01)

(52) U.S. Cl.
 CPC ............ *A61F 4/00* (2013.01); *G06F 3/00* (2013.01); *G06F 3/011* (2013.01); *G06F 3/012* (2013.01); *G06F 3/013* (2013.01); *G06F 3/015* (2013.01); *G06F 3/017* (2013.01); *G06N 20/00* (2019.01); *G09B 5/06* (2013.01); *H04N 7/185* (2013.01); *A61B 5/398* (2021.01); *G02B 27/0093* (2013.01)

(56) References Cited

U.S. PATENT DOCUMENTS

| | | | | |
|---|---|---|---|---|
| 7,930,035 | B2 * | 4/2011 | DiLorenzo | A61B 5/04001 607/45 |
| RE42,471 | E | 6/2011 | Torch | |
| 8,065,154 | B2 * | 11/2011 | Schindler | G10L 13/033 704/260 |
| 9,367,203 | B1 * | 6/2016 | Costello | G06F 3/04815 |
| 10,478,127 | B2 * | 11/2019 | Sampson | A61B 5/0022 |
| 2005/0043644 | A1 * | 2/2005 | Stahmann | A61B 5/0031 600/529 |
| 2005/0076909 | A1 * | 4/2005 | Stahmann | A61B 5/103 128/204.23 |
| 2006/0257827 | A1 * | 11/2006 | Ellenson | G10L 13/033 434/112 |
| 2009/0300503 | A1 * | 12/2009 | Suhm | G10L 13/00 715/733 |
| 2010/0280403 | A1 * | 11/2010 | Erdogmus | A61B 5/0484 600/545 |
| 2011/0161067 | A1 * | 6/2011 | Lesher | G06F 17/241 704/1 |
| 2011/0161073 | A1 * | 6/2011 | Lesher | G06F 17/2795 704/10 |
| 2011/0257977 | A1 * | 10/2011 | Greenberg | G06F 3/167 704/271 |
| 2011/0316880 | A1 * | 12/2011 | Ojala | G06T 19/006 345/633 |
| 2013/0065204 | A1 | 3/2013 | LoStracco et al. | |
| 2013/0089840 | A1 * | 4/2013 | Drane | G09B 19/00 434/219 |
| 2013/0239015 | A1 * | 9/2013 | Forest | A61F 4/00 715/752 |
| 2014/0342321 | A1 * | 11/2014 | Wendt | G09B 7/06 434/156 |
| 2015/0031965 | A1 * | 1/2015 | Visvanathan | A61B 5/0059 600/301 |
| 2015/0153571 | A1 * | 6/2015 | Ballard | G02B 27/0093 345/8 |
| 2015/0220157 | A1 * | 8/2015 | Marggraff | G06F 1/1694 345/156 |
| 2015/0248470 | A1 * | 9/2015 | Coleman | G06F 16/285 707/740 |
| 2017/0123492 | A1 * | 5/2017 | Marggraff | H04N 5/247 |
| 2017/0188823 | A1 * | 7/2017 | Ganesan | G02B 27/0093 |
| 2017/0315825 | A1 * | 11/2017 | Gordon | G06F 16/24575 |
| 2018/0364810 | A1 * | 12/2018 | Parshionikar | G06F 3/012 |

OTHER PUBLICATIONS

International Search Report dated Sep. 13, 2017, in corresponding International Application No. PCT/IB2017/053017; 2 pages.
Written Opinion dated Sep. 13, 2017, in corresponding International Application No. PCT/IB2017/053017; 6 pages.

* cited by examiner

SYSTEM AND METHOD FOR AIDING COMMUNICATION

CROSS-REFERENCE TO RELATED PATENT APPLICATIONS

This application claims the benefit of International Application No. PCT/IB2017/053017, filed May 23, 2017, which claims priority to Indian Application No. 201621025832, filed Jul. 28, 2016, each of which is hereby incorporated by reference in its entirety.

TECHNICAL FIELD

The present disclosure in general relates to aiding communication, and more particularly to system and method for aiding communication using augmentative and alternative communication (AAC) devices.

BACKGROUND

Persons with disabilities, such as subjects with paralysis of muscles are capable of only limited muscle movements, for instance limited head movements and/or eye movements. Examples of such disabilities may include but are not limited to Amyotrophic Lateral Sclerosis (ALS), Locked-in Syndrome (LIS), and so on. In such disabilities, for instance in case of ALS, a subject has a slow progression of paralysis of muscles controlled by peripheral nervous system. Hence, subjects have to take help of wheelchair and cannot move their limbs or any body parts thereof.

Augmentative and alternative communication (AAC) devices can empower these subjects by the use of their remaining functional movements. The AAC devices refer to devices and/or solutions that permit use of electronic devices such as computers by such impaired persons/subjects. The AAC devices includes human computer interface (HCI) that can be used by individuals in speech, vocalizations, gestures, communication actions, specific communication methods or tool. Currently available AAC solutions present limited performance in the presence of involuntary body movement. Moreover, with slow progression of such disabilities, the nature of interaction of the subject with AAC devices changes, and the AAC device may become ineffective in aiding said communication.

SUMMARY

Embodiments of the present disclosure present technological improvements as solutions to one or more of the above-mentioned technical problems recognized by the inventors in conventional systems. For example, in one embodiment, a processor-implemented method for aiding communication is provided. The method includes capturing, from a plurality of sensors, sensor data generated based on an interaction of a subject with an interactive UI, via one or more hardware processors. The plurality of sensors includes one or more body-parts movement tracking sensors for tracking motion of body-parts of the subject and one or more physiological signal sensors for monitoring physiological signals generated during the interaction. Further, the method includes determining, based on the sensor data, a plurality of model parameters indicative of characteristics of the subject related to the interaction, via the one or more hardware processors. Furthermore, the method includes controlling navigation at the interactive UI based on the plurality of model parameters, via the one or more hardware processors.

In another embodiment, a system for aiding communication is provided. The system includes one or more memories storing instructions; and one or more hardware processors coupled to the one or more memories. The one or more hardware processors are configured by said instructions to capture, from a plurality of sensors, sensor data generated based on an interaction of a subject with an interactive UI. The plurality of sensors includes one or more body-parts movement tracking sensors for tracking motion of body-parts of the subject and one or more physiological signal sensors for monitoring physiological signals generated during the interaction. Further, the one or more hardware processors are configured by said instructions to determine, based on the sensor data, a plurality of model parameters indicative of characteristics of the subject related to the interaction. Furthermore, the one or more hardware processors are configured by said instructions to control navigation at the interactive UI based on the plurality of model parameters.

In yet another embodiment, a non-transitory computer-readable medium having embodied thereon a computer program for executing a method for aiding communication is provided. The method includes capturing, from a plurality of sensors, sensor data generated based on an interaction of a subject with an interactive UI, via one or more hardware processors. The plurality of sensors includes one or more body-parts movement tracking sensors for tracking motion of body-parts of the subject and one or more physiological signal sensors for monitoring physiological signals generated during the interaction. Further, the method includes determining, based on the sensor data, a plurality of model parameters indicative of characteristics of the subject related to the interaction, via the one or more hardware processors. Furthermore, the method includes controlling navigation at the interactive UI based on the plurality of model parameters, via the one or more hardware processors.

BRIEF DESCRIPTION OF DRAWINGS

The detailed description is described with reference to the accompanying Figures. In the Figures, the left-most digit(s) of a reference number identifies the Figure in which the reference number first appears. The same numbers are used throughout the drawings to refer like/similar features and components.

DETAILED DESCRIPTION

Figure 1:
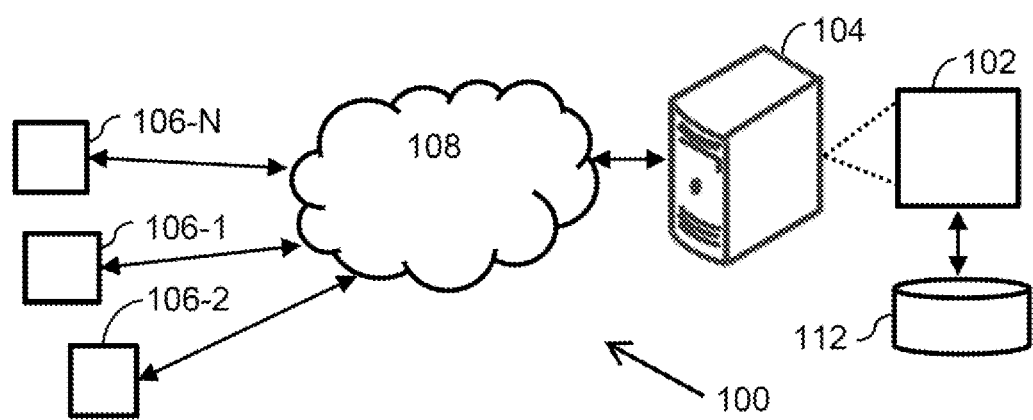
FIG. 1 illustrates a networking environment implementing aiding communication of subjects, in accordance with an embodiment of the present subject matter.

The AAC devices empower subjects with paralysis of muscles controlled by peripheral nervous system, by the use of their remaining functional movements. Examples of such disabilities may include ALS, LIS, and so on. In case of a subject suffering from ALS, the degradation of motion of body parts happen progressively and eventually stops. Since the condition of the subject changes/deteriorates progressively, it is important to track the body movements (control and coordination) at each stage so as to enable the subject to communicate. For example, in the initial stages of ALS, the subject may be able to move certain body parts substantially, for instance, the subject may exhibit head movement and tongue movement. Additionally, the speech also degrades and finally stops. However, such movement goes away eventually. For example, with the progression of ALS, the subject's movements may be limited to eyeball movement, eye blinks, minute vibration of vocal track and certain facial muscles. In order to enable communication of such subjects, it is pertinent that the subject's body movements (which are continuously varying with time) can be effectively monitored by the ACC device. Currently AAC devices, however, provide limited performance due to continuous progression of subject's paralysis.

Various embodiments of the present disclosure provide method and system that may aid in effective communication of/with the subjects during continuous progression of paralysis of the muscles that are controlled by the peripheral nervous system. For example, the embodiments provide an adaptable system capable of adapting itself automatically to remain personalized as the state of the subject changes with time. In an embodiment, the disclosed system includes a plurality of sensors that are capable of sensing subject's movements and thoughts using certain wearable and/or camera sensors to navigate texts, words, sentences, on an interactive user interface (UI), and then communicate to others using a computer and a display device. The system may include modules for processing the information received from various sensors, in a manner that said information may present a personalized communication mechanism for the subject during the progression of the paralysis. Additionally, the system includes a feedback mechanism to determine validity of sensed data, and update the system based on the validated data. A detailed description of the above described system for aiding communication is shown with respect to illustrations represented with reference to FIGS. 1 through 10.

The method(s) and system(s) for aiding communication with subjects are further described in conjunction with the following figures. It should be noted that the description and figures merely illustrate the principles of the present subject matter. It will thus be appreciated that those skilled in the art will be able to devise various arrangements that, although not explicitly described or shown herein, embody the principles of the present subject matter and are included within its spirit and scope. Furthermore, all examples recited herein are principally intended expressly to be only for pedagogical purposes to aid the reader in understanding the principles of the present subject matter and the concepts contributed by the inventor(s) to furthering the art, and are to be construed as being without limitation to such specifically recited examples and conditions. Moreover, all statements herein reciting principles, aspects, and embodiments of the present subject matter, as well as specific examples thereof, are intended to encompass equivalents thereof.

FIG. 1 illustrates a network environment 100 implementing a system 102 for aiding communication, according to an embodiment of the present subject matter. The system 102 is configured to aid communication with subjects suffering from paralysis of muscles that are controlled by the peripheral nervous system. In an embodiment, the system 102 receives sensor data from a plurality of sensors that are capable of monitoring subject's movements. The system automatically processes the sensor data to perform analysis of the subject's movements, and presents result of such analysis on a configurable user interface. The system 102 may be embodied in a computing device, for instance a computing device 104.

Although the present disclosure is explained considering that the system 102 is implemented on a server, it may be understood that the system 102 may also be implemented in a variety of computing systems, such as a laptop computer, a desktop computer, a notebook, a workstation, a cloud-based computing environment and the like. In one implementation, the system 102 may be implemented in a cloud-based environment. It will be understood that the system 102 may be accessed by multiple users through one or more user devices 106-1, 106-2 . . . 106-N, collectively referred to as user devices 106 hereinafter, or applications residing on the user devices 106. Examples of the user devices 106 may include, but are not limited to, a portable computer, a personal digital assistant, a handheld device, a Smartphone, a Tablet Computer, a workstation and the like. The user devices 106 are communicatively coupled to the system 102 through a network 108. Herein, the users of the user-devices 106 may include one or more of the subjects, subject's caregivers, doctors, and so on.

In an embodiment, the network 108 may be a wireless or a wired network, or a combination thereof. In an example, the network 108 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 108 may include a variety of network devices, including routers, bridges, servers, computing devices, storage devices. The network devices within the network 108 may interact with the system 102 through communication links.

As discussed above, the system 102 may be implemented in a computing device 104, such as a hand-held device, a laptop or other portable computer, a tablet computer, a mobile phone, a PDA, a smartphone, and a desktop computer. The system 102 may also be implemented in a workstation, a mainframe computer, a server, and a network server. In an embodiment, the system 102 may be coupled to a data repository, for example, a repository 112. The repository 112 may store data processed, received, and generated by the system 102. In an alternate embodiment, the system 102 may include the data repository 112. The components and functionalities of the system 102 are described further in detail with reference to FIG. 2.

Figure 2:
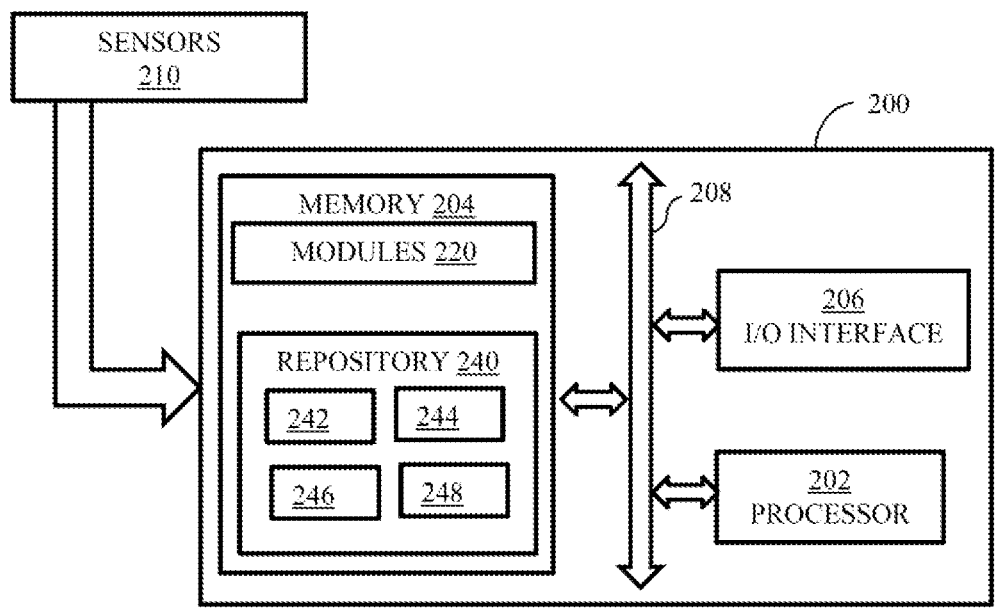
FIG. 2 illustrates a block diagram of a communication aiding system, in accordance with an example embodiment.

FIG. 2 illustrates a block diagram of a communication aiding system 200, in accordance with an example embodiment. The communication aiding system 200 (hereinafter referred to as system 200) may be an example of the system 102 (FIG. 1). In an example embodiment, the system 200 may be embodied in, or is in direct communication with the system, for example the system 102 (FIG. 1). In an embodiment, the system facilitates in facilitating communication with subjects suffering from paralysis of the muscles that are controlled by the peripheral nervous system. The system 200 includes or is otherwise in communication with one or more hardware processors such as a processor 202, at least one memory such as a memory 204, and an I/O interface 206. The processor 202, memory 204, and the I/O interface 206 may be coupled by a system bus such as a system bus 208 or a similar mechanism.

The I/O interface 206 may include a variety of software and hardware interfaces, for example, a web interface, a graphical user interface, and the like The interfaces 206 may include a variety of software and hardware interfaces, for example, interfaces for peripheral device(s), such as a keyboard, a mouse, an external memory, a camera device, and a printer. Further, the interfaces 206 may enable the system 102 to communicate with other devices, such as web servers and external databases. The interfaces 206 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 206 may include one or more ports for connecting a number of computing systems with one another or to another server computer. The I/O interface 206 may include one or more ports for connecting a number of devices to one another or to another server.

The I/O interface 206 includes a self-adaptive interface and interactive UI and is capable of determining context of the communication. In an embodiment, the I/O interface 206 presents selection of certain words, sentences, symbols, and so on, to generate communication phrase(s) for aiding the communication. In an embodiment, the I/O may include an on-screen keyboard having a configurable layout.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the hardware processor 202 is configured to fetch and execute computer-readable instructions stored in the memory 204.

The memory 204 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 204 includes a plurality of modules 220 and a repository 240 for storing data processed, received, and generated by one or more of the modules 220. The modules 220 may include routines, programs, objects, components, data structures, and so on, which perform particular tasks or implement particular abstract data types.

The repository 240, amongst other things, includes a system database 242 and other data 244. The other data 244 may include data generated as a result of the execution of one or more modules in the modules 220. The repository 240 is further configured to maintain a training data 246 and sensor data 248.

According to the present subject matter, the system 200 aids in communication with subjects. In an embodiment, the system 200 is caused to track body part movements of the subject using a plurality of sensors 210. Examples of such bodily movements may include, but are not limited to, head movement, eyeball movement, eye blinks, and so on. The system 200 may track the bodily movements and/or certain physiological signals based on an interaction of the subject with the plurality of sensors 210. Examples of the plurality of sensors 210 may include, but are not limited to, an Inertial Motion Unit (IMU), an electroencephalogram (EEG) sensor, eye tracking sensor, physiological sensors, and so on.

The IMU may be worn on subject's head, for instance on a cap to capture IMU derived parameters including acceleration, angular rate, and sometimes magnetic field surrounding subject's body. The IMU sensor may include 3-axis accelerometer, 3-axis gyroscope and magnetometer for capturing the IMU derived parameters. The EEG sensor may be embodied in an EEG headset, for instance in a 5 lead EEG device, and is configured to capture IMU data and the EEG data received from the subject. The eye tracking sensors are capable of tracking subject's eye movements, and can be utilized to capture the gaze of the eyeball and eye blink of the subject. In an embodiment, raw signal co-ordinates (X, Y) of the eye tracking sensor can be captured to locate where the subject is looking on a display screen of the I/O interface. Alternately, a wearable Electrooculogram (EOG) sensor can be used to detect the eyeball movement and eye blinks and then translate the same to mouse movement of keyboard entries. Additionally, the system 200 may track and obtain certain physiological signals (Galvanic Skin Response, Photoplethysmogram, and the like) taken via physiological sensors from the subjects to obtain physiological data as additional feedback on the mental workload and stress during performing the interaction with the subject. The physiological signals may include sensed movement intention obtained from brain signals of the subject.

In an embodiment, IMU data, EEG data, the eyeball movement data (including data obtained from eye tracking sensor and/or EOG sensor), and physiological data may hereinafter be collectively referred to as sensor data. The sensor data may be stored in the memory 204 of the system 200. The system 200 may be caused to process the sensor data to obtain processed sensor data.

The system 200 is caused to determine a plurality of model parameters based on the sensor data. The plurality of model parameters are indicative of characteristics of the subject related to the interaction of the subject with the plurality of sensors 210. For example, the sensor data derived from the accelerometer and gyroscope may facilitate in determination of shape and energy in various direction X, Y and Z. Based on said determination, the direction of movement of the subject's head is determined. The ratio of the energy values may form the model parameters. An example of graphs illustrating energy variation for different head movements is presented with reference to FIGS. 7A and 7B. As will be appreciated from the later description herein, the plurality of model parameters facilitate in controlling interaction of the subject with an interactive UI. For example, the ratio of energy values may change with time, as due to deterioration of subject's ability to move (with progression of disease), the subject's head movement may also change. Hence the system 200 may be caused to track the change in value of said ratio over a period of time, and adapt the changed or updated value of the ratio to control the interaction of the subject with the interactive UI, as will be explained later.

In another embodiment, based on eye gaze the location of the screen co-ordinates are determined. The ability to move the eye degrades over time for subjects suffering from ALS, and therefore, the duration for which the subject can hold eyes on a specific region before moving to the next location changes. Additionally, the speed of movement of the eye gaze also changes with time. Herein, the speed of movement and the duration for which the subject can hold eye gaze at a specific location are the model parameters. Hence, the system 200 is caused to monitor the change in duration for which the subject's gaze is held at a particular region or location on the UI, and speed of said movement. The system 200 is the caused to adapt the changed or updated values of said duration and speed with time based on the changing ability of the subject, and controls the interactive UI based on said changed or update values.

In an embodiment, based on the plurality of model parameters, the system 200 is caused to automatically present a configurable and interactive user interface having attributes that may be utilized for communicating with the subject. For instance, the user interface may be controlled to select sentences, words, symbols, other available user choices, and so on, to thereby enable the communication with/for the subject. Herein, it will be appreciated that the UI is a context based intelligent UI, as the UI is presented based on a selection of certain words, sentences, symbols, and so on, to generate the communication phrase. The set of words or sentences that may be presented on a display screen may be based on time (morning, evening, and so on) of the day, and/or day (e.g. Sunday) of week and/or festive occasions (birthday, family gathering, and so on), and/or location (visiting doctor's place, tourist location etc.) and/or emergency scenarios (phone numbers etc.). The communication can also be done using the on-screen keyboards. In an embodiment, the system 200 may be caused to present a configurable keyboard layout for the purpose of communication, as described below.

In a configurable keyboard layout, the layout of the words and/or sentences may be automatically configurable based on the direction of motion (left-right, up-down, diagonal, and so on) that the subject is comfortable with. In an embodiment, the configuration of keyboard layout may be adapted as the condition of the patient changes with time, since with progression of medical condition the subject may lose some or substantial movement capability thereof. The changing medical condition of the subject may be determined based on the model parameters that may be determined continuously during the usage of the system 200 by the patient and caregivers of the patient, and the layout of keyboard may adapt accordingly.

In an embodiment, the layout of the keyboard (QWERTY, Hierarchical, and so on) may also adapt accordingly. For example, if the subject is able to move head in horizontal direction then the subject can use such head movement to navigate (hence select words) horizontally on the UI. But upon progression of the paralysis, due to limited horizontal movement of the subject's head, the system 200 may cause the layout to be oriented vertically to aid the subject. Herein, the system 200 is capable of automatically learning user capability or control, and performs the self-adaptation. The self-adaptation of the system 200 can be facilitated in an online learning or offline learning, as explained below.

In an embodiment, the system 200 may be a self-adapted system that is capable of adapting to the changes in the state of the subject. For the purpose of adaptation, the system 200 can be trained based on learning of the state/condition of the subject using motion and/or physiological conditions. As described previously, the system 200 is caused to monitor subject's motion and/or physiological conditions using the plurality of sensors, and based on said monitoring, the system 200 determines the plurality of model parameters. The system 200 utilizes the plurality of model parameters for training a model.

In an embodiment, the system is trained in an offline learning mode. In the offline learning and adaptation of the system 200, the system 200 may be caused to record various bodily movements of the subject, such as head movement, eyeball movement, and so on in certain directions based on predefined templates (for example, up-down direction, left-right direction, and so on), to obtain a training data. The system 200 is caused to analyse said training data to obtain the plurality of model parameters that includes the information about the characteristics of the subjects related to motion and thought process of the subject, in order to interact using the system 200. The system 200 may be caused to validate the model parameters. Upon verification, the system 200 can be utilized for enabling the communication. In an embodiment, the system 200 may include a training and adaptation module to update the instruction templates and control the determination and verification of the plurality of model parameters. Herein, it will be noted that the system 200 may be trained in the offline learning mode during an initial working state of the system 200. In an example embodiment, the system 200 may store a subject's profile upon initial training of the system in the offline learning mode. However, if upon creation of the subject's profile, the subject is not satisfied with said profile, the subject may be allowed to reset the stored profile. In such a scenario, offline learning mode may be initiated again. An example process flow for offline training and adaptation is illustrated and described further with reference to FIG. 3.

Additionally or alternatively, the system 200 can be trained in an online learning mode. In online training mode, during natural interactions with an initial working state of the system 200, the sensor data is continuously monitored to determine any consistent change in the interaction of the subject with the UI, and adapts the plurality of model parameters accordingly. Herein, the term 'consistent change' may refer to change in interaction of the subject with the system (and/or UI) for a threshold number of times. For instance, a subject may provide a response in a certain manner. Now with progression of medical condition of the subject, the response of the subject may change from the previous response. The system may verify, for the threshold number of times, the response of the subject to validate whether the changed response is consistent during the threshold number of times or not. If the response is determined to be consistent for the threshold number of times, the system may learn that the subject's response has changed (for example, due to progression of the medical condition of the subject), and may adapt itself accordingly. For example, a subject may nod head vertically, and corresponding sensor readings may be $k*10^3$ unit. The unit may be in degrees/sec. Here k is a real number, and the value of k observed may change with the amount of head motion. Also, the value of k may also depend on the direction of head movement. Herein, the sensor(s) utilized for capturing the readings (or the sensor data) may include 3-axis accelerometer and 3-axis gyroscope. Based on the observation of the values of k, the system 200 may learn a change in the state of the subject. In an instance of confusion state, for example, where the system 200 is no more able to detect the head motion for a given threshold, the system 200 may prompt for confirmation for an additional head movement. Based on the observed value of the additional head movement, the one or more model parameters may be adapted. In the present example, said adaptation of the model parameters depends on the value of k. An example process flow for online training and adaptation is illustrated and described further in detail with reference to FIG. 4.

In an embodiment, the system 200 may receive an active audio and/or visual feedback to provide information about an amount of involvement of the subject in terms of required motion or thought process. Said information can be utilized by the system 200 during offline learning as well as during normal interaction (for example, during online learning) for the purpose of training. In case of offline training, the subject may be asked to move the head or cheek muscle or eyeball in certain direction. Once the subject performs the motion, the signal of IMU sensor is analysed to detect the amount of motion achieved. Said amount of motion is provided as a visual level or audio input to the system 200 to indicate whether the subject is doing well or need to try better. In case of online training, the frequency of the feedback may vary and need not be continuously done. The feedback may be provided once in a day or as determined by the system.

In an embodiment, in case the physiological signals are utilized for navigation on the display screen, for example during advanced stages of the paralysis, when the subject is unable to effect bodily movements, the subject's motion (that is imagined by the subject), can be captured by the system by using motor imagery related brain signals of subject can used to detect the direction of the motion imagined. In an embodiment, said direction can be detected by EEG signals and the intensity of the imagination can be given as an audio and/or visual feedback on the UI.

Figure 3:
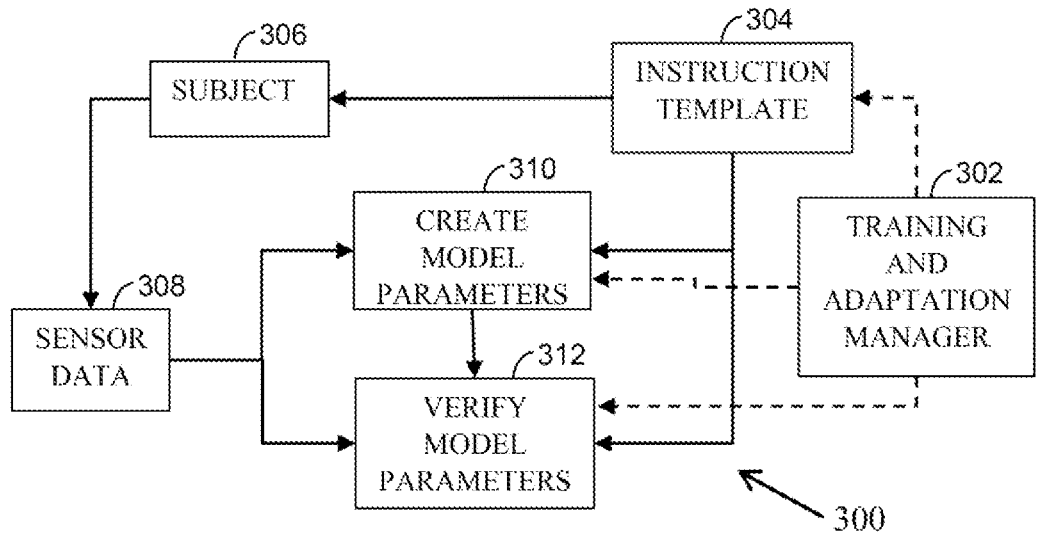
FIG. 3 illustrates an example process flow for offline training and adaptation of the communication aiding system, in accordance with an example embodiment.

FIG. 3 illustrates an example process flow 300 for offline training and adaptation of the communication aiding system 200 of FIG. 2 in accordance with an example embodiment. In an embodiment, the communication aiding system may include a training and adaptation manager 302 for the offline training and adaptation of the communication aiding system. As illustrated in FIG. 3, and also described previously, the system 200 is caused to prompt a subject to perform a plurality of known tasks. The plurality of known tasks includes interacting with the interactive UI. For example, the subject would be asked to move the body parts (head, eyeball, and so on) in certain direction based on predefined templates (up-down, left-right etc.). In an embodiment, the plurality of known tasks may be stored in an instruction template 304. Based on the instructions, the subject may perform said know tasks at 306.

During the time when the subject performs said known tasks, the system 200 captures a sensor data generated by the plurality sensors (such as sensors 210 of FIG. 2). Herein, the sensors capture movements of the subject during the performance of performs said known tasks as sensor data at 308. The training and adaptation manager 302 utilizes the captured sensor data and the instruction template to create model parameters at 310, and verify said model parameters at 312. For example, the subject may be asked to move the body parts (head, eyeball etc.) in certain direction based on predefined templates (up-down, left-right etc.). During this time the sensor data is collected and analysed to create the model parameters which would store the information about the characteristics of the subjects related to motion and thought process in order to interact using the system 200. A validation of the training is performed to verify the model.

Once the model parameters are verified, the system 200 enters the execution phase for enabling the communication. The training and adaptation manager 302 may update the instruction templates and controls the creation and verification and verification of model parameters.

Figure 4:
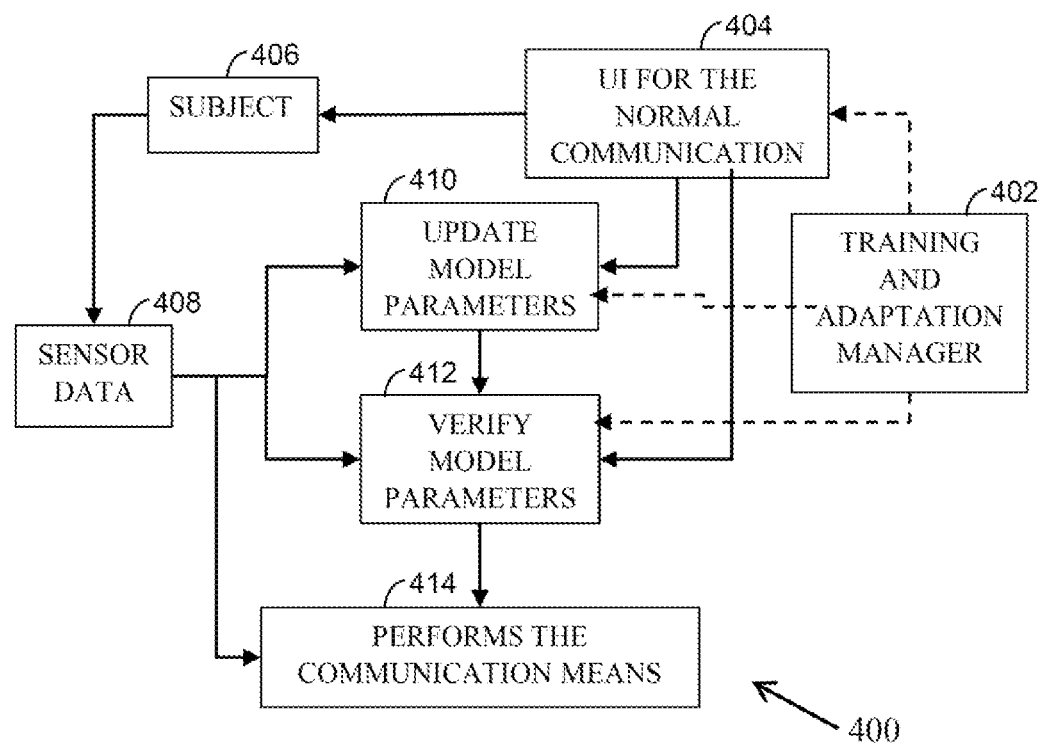
FIG. 4 illustrates an example process flow for online training and adaptation of the communication aiding system, in accordance with an example embodiment.

FIG. 4 illustrates an example process flow 400 for online training and adaptation of the communication aiding system 200 of FIG. 2, in accordance with an example embodiment. In an embodiment, the communication aiding system may include a training and adaptation manager 402 for the online training and adaptation of the communication aiding system.

As illustrated in FIG. 4, the system 200 includes a UI for enabling the subject to perform routine tasks through normal communication, at 404. The plurality of tasks includes interacting with the interactive UI by movement of body parts (such as head, eyeball and so on) in certain directions for communication, at 406. During the time when the subject performs said routine tasks, the system 200 captures a sensor data generated by the plurality sensors (such as sensors 210 of FIG. 2) at 408. Herein, the sensors capture movements of the subject during the performance of performs said tasks as sensor data at 408. The training and adaptation manager 402 monitors the captured sensor data (generated at 408) generated based on the interaction of the subject with the interactive UI. If upon a comparison of the captured sensor data and the training data, the training and adaptation manager 402 determines a consistent change in the interaction, the training and adaptation manager 402 automatically updates the model parameters at 410, and verifies said model parameters at 412. An example architecture of the system for aiding communication is described further with reference to FIG. 5.

Figure 5:
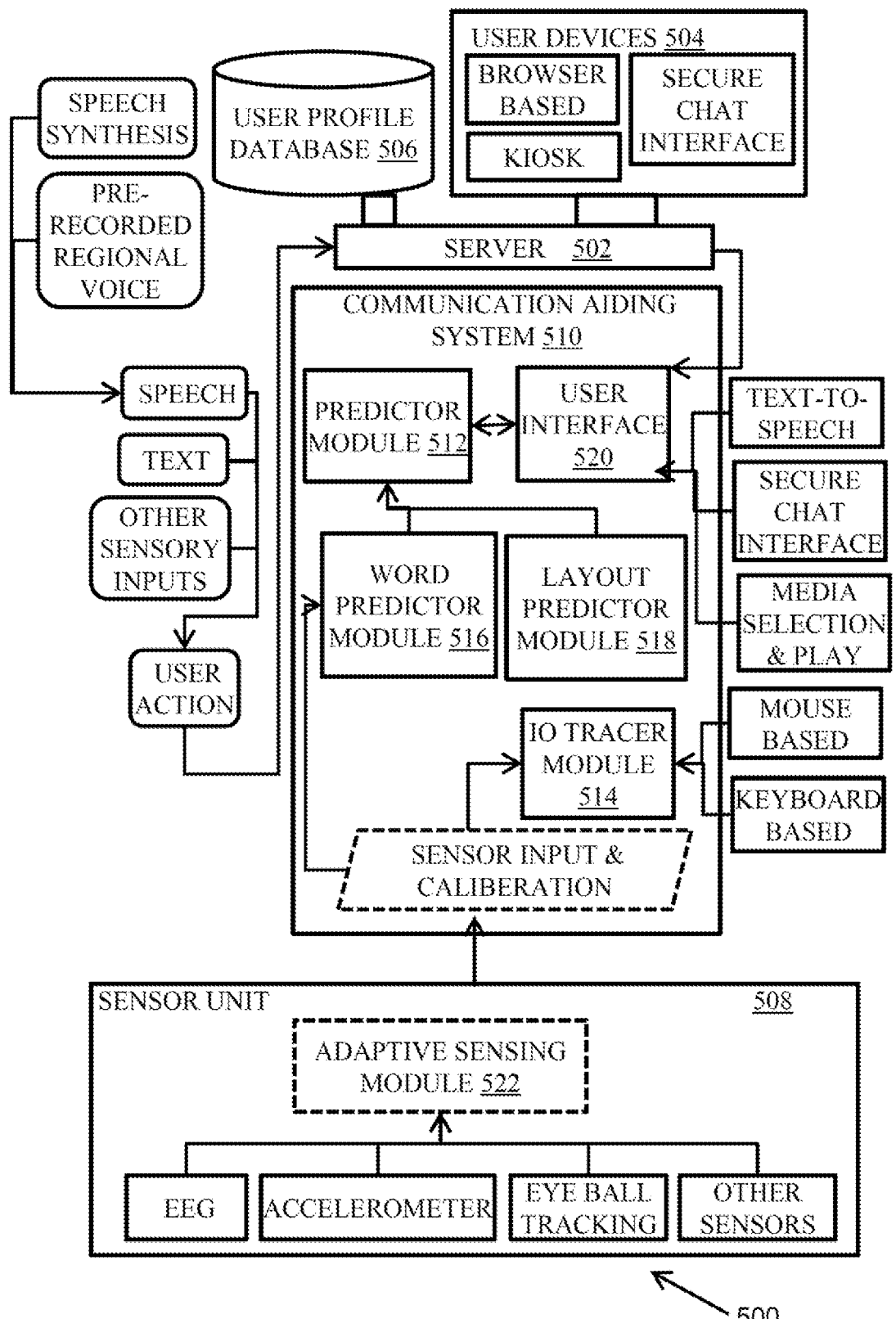
FIG. 5 illustrates a detailed system implementation of the system for aiding communication, in accordance with an example embodiment.

FIG. 5 illustrates example system architecture for aiding communication for subjects, in accordance with an example embodiment. The architecture 500 for aiding communication for subjects is shown to include a server 502, user devices 504, a user profiles database 506, a sensor unit 508, and a communication aiding system 510.

The server 502 may integrate various logical divisions associated with aiding the communications for subjects. In an embodiment, the server 502 may include or may be communicably coupled with a central distributed repository that may receive and store various data. For instance, the server 502 may include or may be communicably coupled with the user-profile database 506 for storing a plurality of profiles of a plurality of subjects. A user-profile associated with a subject may include various attributes such as User Information, User Disease Progression History, Layout Arrangement, Word Predictor Dictionary, Regional Audio Speech preference corresponding to different subjects, and so on. The user profile database facilitates in providing a personalized experience to an individual user or subject, so that whenever user logs-in from any device, the user may a personalized user interface.

The server 502 may be communicably coupled to the plurality of user devices 504 (hereinafter referred to as user devices 504). The user devices 504 are similar to the user devices 106 of FIG. 1. The user devices 504 enables a plurality of users to access the server 502. Herein, the users of the user-devices 504 may include one or more of the subjects, subject's caregivers, doctors, and so on. Examples of the user devices 504 may include, but are not limited to, a portable computer, a personal digital assistant, a handheld device, a Smartphone, a Tablet Computer, a workstation and the like. The user devices may enable access of the server through, for example, kiosk, browser based applications, cell phone applications, and so on.

The sensor unit 508 may include a plurality of sensors for monitoring or tracking user movements. For instance, the sensor unit may include Electroencephalogram (EEG), Electromyogram (EMG), an accelerometer, an eye ball tracking sensor, and other such sensors. The plurality of sensors may facilitate in sensing for aiding communication. The sensor unit 508 includes an adaptive sensing unit 522 for facilitating adaptive sensing of the model parameters. The adaptive sensing unit 522 may monitor the values of the model parameters provided by the sensors over a period of time during which the condition of the subject may change. For example, the adaptive sensing unit 522 monitors the sensor data derived from the accelerometer and gyroscope to determine shape and energy in various direction X, Y and Z. Based on said determination, the direction of movement of the subject's head is determined. The ratio of the energy values forms the model parameters. Due to deterioration of subject's ability to move (with progression of disease), the subject's head movement may also change, thus the ratio of energy values may change with time, and the accordingly the values of model parameters changes with time. Hence, the adaptive sensing unit 522 tracks the change in value of said ratio over a period of time, and adapts the changed or updated value of the ratio to control the interaction of the subject with the interactive UI.

Additionally or alternatively, the adaptive sensing unit 522 monitors the sensor data derived based on the eye gaze of the subject, and accordingly the co-ordinates are determined. For example, the sensor data may include duration for which the subject can hold eyes on a specific region before moving to the next location, speed of movement of the eye gaze, and so on. Herein, the speed of movement and the duration for which the subject can hold eye gaze at a specific location are the model parameters. As the ability to move the eye degrades over time for subjects suffering from ALS, and therefore, the duration for which the subject can hold eyes on a specific region before moving to the next location changes. Additionally, the speed of movement of the eye gaze also changes with time. The adaptive sensing unit 522 may monitor a change in said sensor data over a period of time, and adapt to the changed or updated values of said duration and speed with time based on the changing ability of the subject to control the interactive UI. The output, for example, the updated values of the model parameters of the sensor unit 508 may include a sensor data that can be utilized for predicting the user behaviour, so as to aid communication with the subject.

In an embodiment, the output of the sensor unit 508 is provided as input to the communication aiding system 510 (hereinafter referred to as the system 510). In an embodiment, the system 510 may include a predictor module 512 and an IO tracer module 514. The predictor module 512 receives sensor data from the sensor unit, and based on the sensor data and a training data, predicts possible choices to be presented on the UI for ease of the subject. The possible choices may be indicative of intention of the subject for controlling the display on the UI. In an embodiment, the predictor module 512 may include a word predictor module 516 for predicting the words that the subject may be trying to convey through bodily movements thereof. Additionally or alternatively, the predictor module 512 may include a layout predictor module 518 for predicting a layout to be presented to the subject for aiding the communication.

Figure 7A:
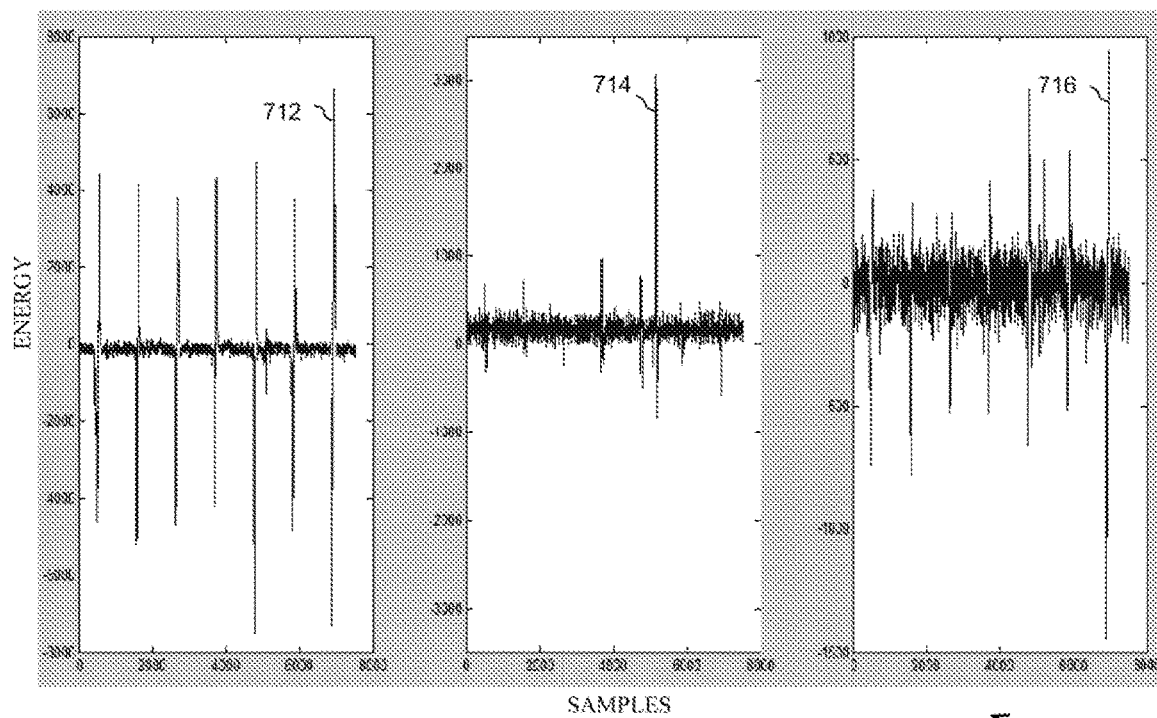
FIGS. 7A and 7B illustrate graphs for energy variation corresponding to different head movements of a subject, in an example embodiment.
Figure 7B:
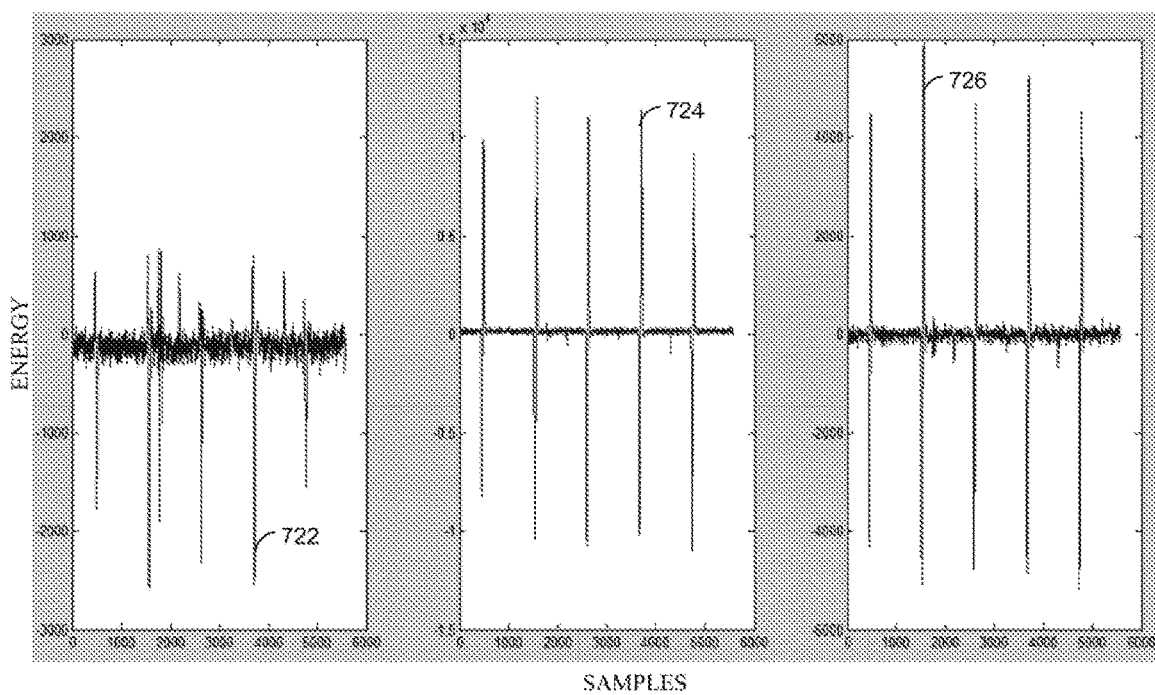

The predictor module 512 may be communicably coupled to a UI module 520. In addition, the IO tracer module 514 may receive sensor data from the sensor unit pass the sensor data from respective sensors to the User Interface in form of the basic IO Device control such as Mouse or Keyboard. For example, for a sensor such as a gyroscope sensor, various vertical and horizontal rotation movements of subject's head may be sensed by the gyroscope sensor. The sampling rate may be assumed to 50.2 Hz. The time domain signal for a 3-axis gyroscope signal can be analysed to detect the vertical and horizontal movements. In this case, the signal power may be measured every 1 sec window. When the power is more than a predefined threshold then the movement is detected. One axis is used to detect horizontal movement and another one is used for vertical movement. The third axis may not be used. The movement information is used to control the mouse; navigate texts (sentences) as shown in FIG. 7A, FIG. 7B, FIG. and 7C; and type characters using onscreen keyboards (as shown in FIG. 8).

The UI module 520 may be similar to the I/O interface 206 of FIG. 2. The UI module 520 is capable of presenting the output of the predictor module 512. In an embodiment, the UI module 520 may be communicably coupled to the server 502 so as to provide an interface between the subject and the server 502. The UI module 520 may include one or more of modules including but not limited to, a text-to-speech converter, chat interface, media player, sensor controller, and so on. In an embodiment, the commands through user interface can then be converted into user actions by centralized server. A user action can be pronunciation of text typed by user (speech), feeding text to any utility (such as email, web-browsers, and so on) or simple sensory control such as controlling wheel-chair. In an example embodiment, the UI may highlight a detected region thereon and playout a sound accordingly for the purpose of communication. For example, in order to enable the text to speech conversion for playout of the sound, voice (texture) sample for the subject can be collected when the subject has that ability. Said texture can be used to playout the sound. In an example embodiment, the system 200 may include piezo electric sensors to capture vibrations of subjects' vocal cord.

In an example embodiment, various items may be displayed on the UI including words, sentences which are either automatically highlighted in round-robin manner and the selection may be done by movement/vibration means. Alternately, the items can be selected and highlighted solely by movement/vibration means. In an embodiment, the UI may include local language and demographic specific support. The UI may also include on-screen keyboard. The examples of UIs are illustrated with reference to FIGS. 7A-7C and FIG. 8.

Figure 6:
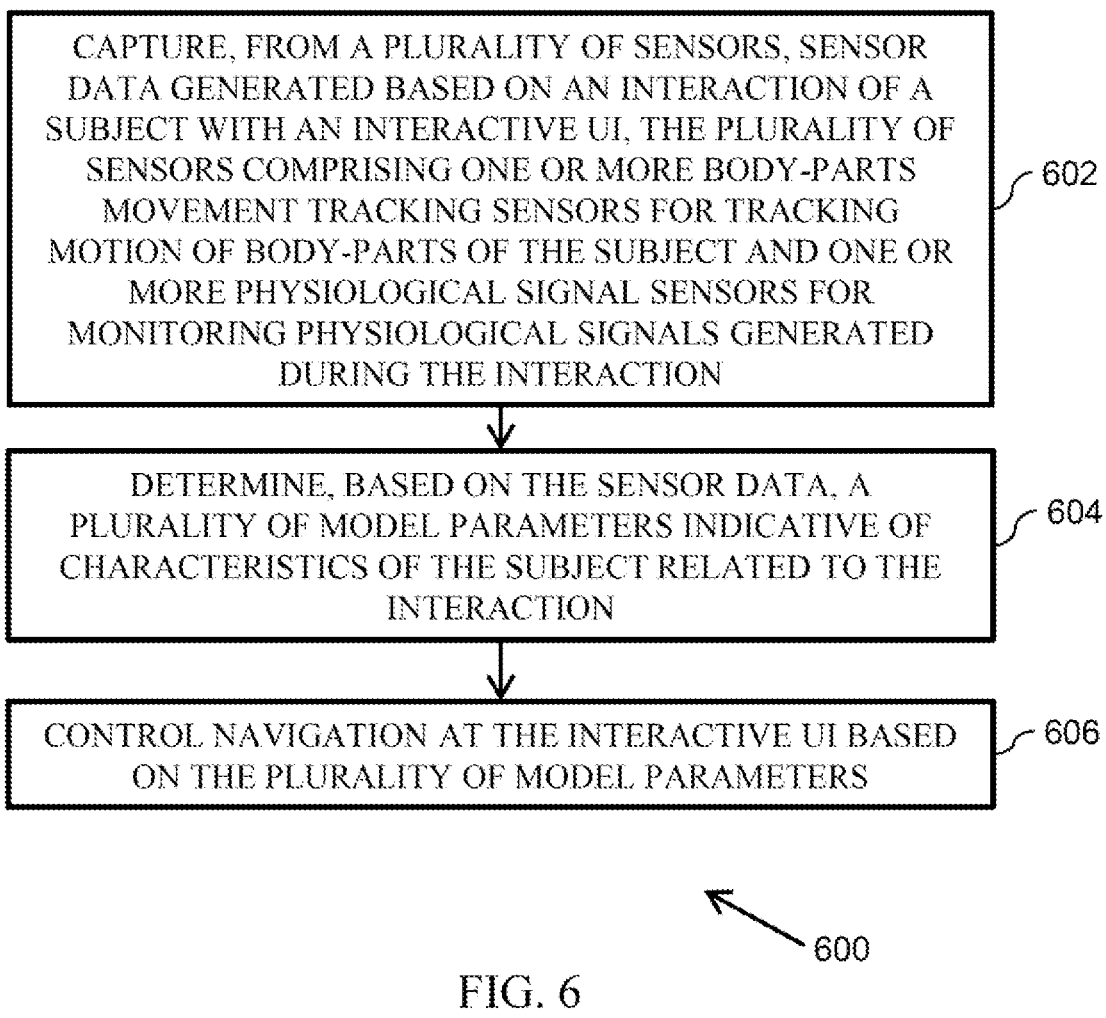
FIG. 6 illustrates a flow-diagram of a method for aiding communication, in accordance with an example embodiment.

FIG. 6 illustrates a flow diagram of a processor-implemented method 600 for aiding communication in accordance with an example embodiment. The method 600 may be described in the general context of computer executable instructions. Generally, computer executable instructions can include routines, programs, objects, components, data structures, procedures, modules, functions, etc., that perform particular functions or implement particular abstract data types. The method 600 may also be practiced in a distributed computing environment where functions are performed by remote processing devices that are linked through a communication network. The order in which the method 600 is described is not intended to be construed as a limitation, and any number of the described method blocks can be combined in any order to implement the method 600, or an alternative method. Furthermore, the method 600 can be implemented in any suitable hardware, software, firmware, or combination thereof. In an embodiment, the method 600 depicted in the flow chart may be executed by a system, for example, the system 200 of FIG. 2. In an example embodiment, the system 200 may be embodied in a computing device, for example, the computing device 110 (FIG. 1).

At 602, the method includes capturing, from a plurality of sensors, sensor data generated based on an interaction of a subject with an interactive UI. The plurality of sensors includes one or more body-parts movement tracking sensors for tracking motion of body-parts of the subject and one or more physiological signal sensors for monitoring physiological signals generated during the interaction. Examples of such bodily movements may include, but are not limited to, head movement, eyeball movement, eye blinks, and so on. Examples of the plurality of sensors may include, but are not limited to, an Inertial Motion Unit (IMU), an electro-encephalogram (EEG) sensor, eye tracking sensor, physiological sensors, and so on. At 604, the method includes determining, based on the sensor data, a plurality of model parameters indicative of characteristics of the subject related to the interaction. At 606, the method includes controlling navigation at the interactive UI based on the plurality of model parameters. Various examples of interactive UIs are described further with reference to FIGS. 8A-8C, FIGS. 9 and 10.

FIGS. 7A and 7B illustrate graphs for energy variation corresponding to different head movements of a subject, in an example embodiment. For example, FIG. 7A illustrate a graph 710 for gyroscope energy values in X, Y and Z-direction. The graph 710 represents a variation of samples of sensor data with energy. Herein, the prominent spikes such as spikes 712, 714, 716 with substantial higher energy in X direction indicate the vertical movement of the head of the subject. FIG. 7B illustrate a graph 720 for gyroscope energy values in X, Y and Z-direction. The graph 710 represents a variation of samples of sensor data with energy. Herein, the prominent spikes, such as spikes 722, 724, 726 with substantial high energy in Y direction indicate the sideways (horizontal) movement of head.

Figure 8A:
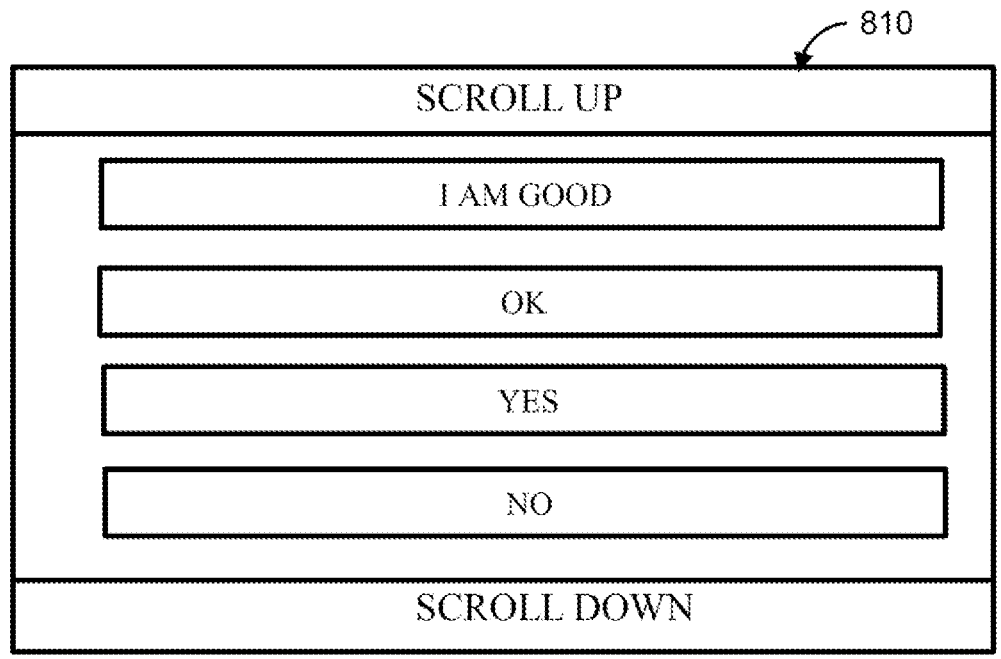
FIGS. 8A-8C illustrates an example UI for aiding communication, in accordance with an example embodiment.
Figure 8B:
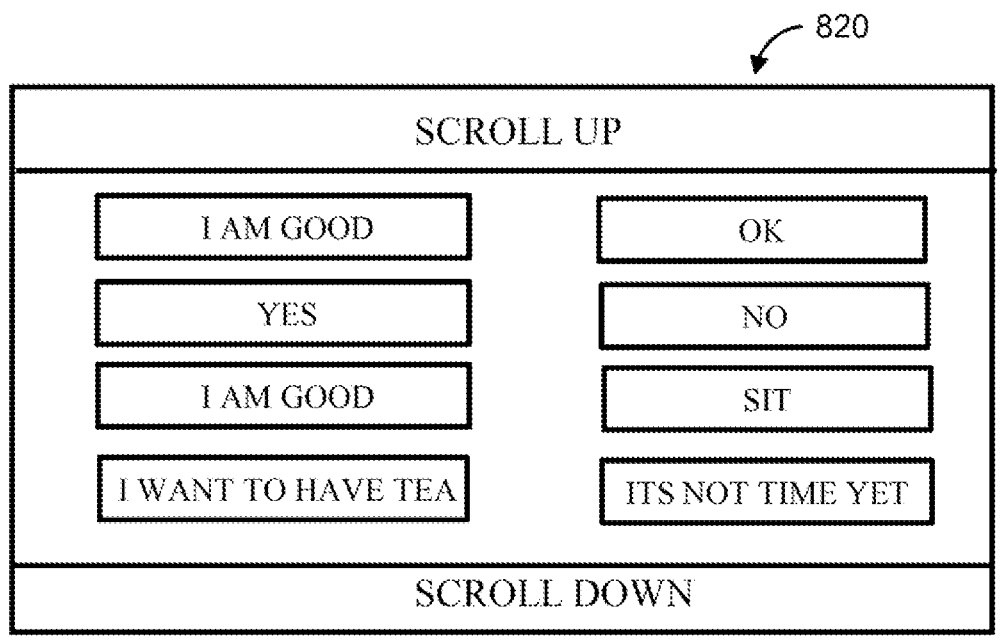
Figure 8C:
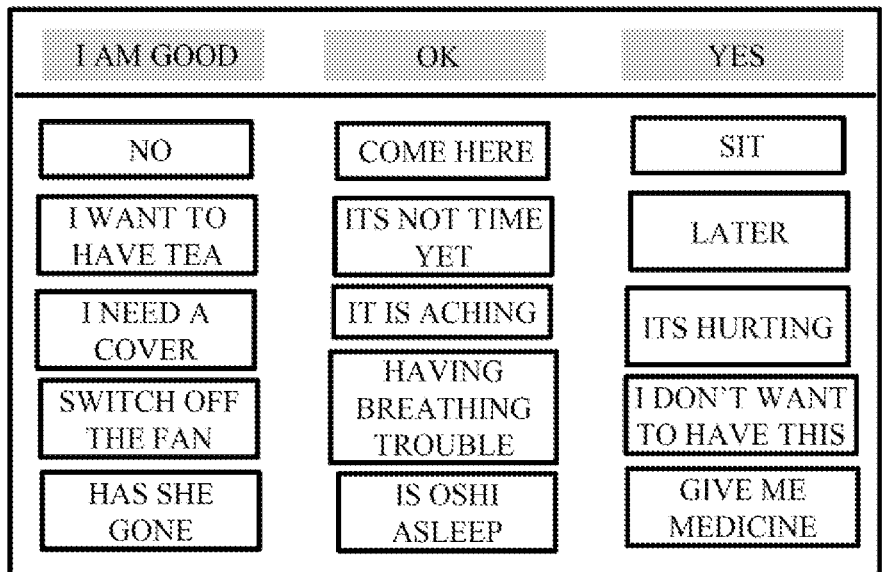

FIGS. 8A-8C illustrates interactive UIs in accordance with various example embodiments. For example, FIG. 8A illustrate interactive UI 810, FIG. 8B illustrate interactive UI 820 and FIG. 8C illustrate interactive UI 830. As illustrated in FIGS. 8A-8C, the interactive user interface is variable according to the needs of the subject and training level of the interactive UI. For example, at first, a single column for novice user may be presented on the UI 810 as illustrated in FIG. 8A. With usage of the device by the subject, the UI may adapt to present the UI with increasing number of predicted suggestions, as illustrated in FIGS. 8B and 8C.

Figure 9:
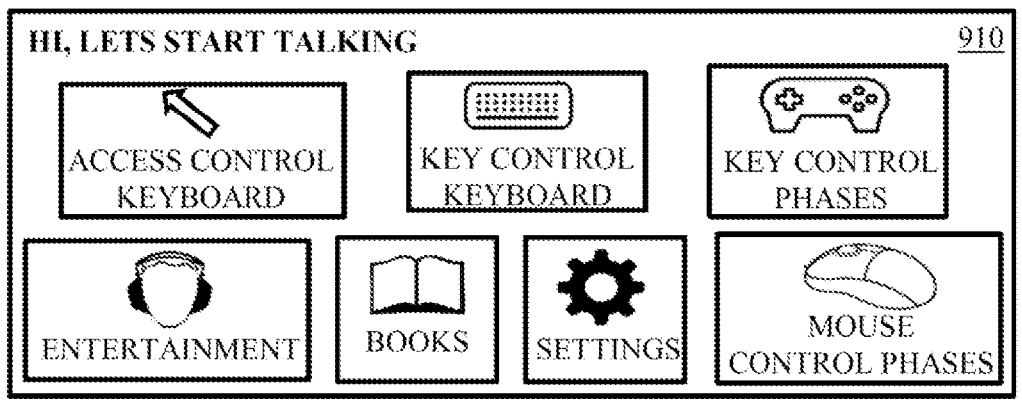
FIG. 9 illustrates screenshots of an example UI for aiding communication, in accordance with another example embodiment.

FIG. 9 illustrate example screenshots of an interactive UI 900, in accordance with various embodiments of the present disclosure. For example, as soon as the system launches the UI, a first screen 910 may appears. The screen 910 includes various options for interaction with the UI. For instance, the screen includes options such as communication, entertainment mode to listen music or watch movie, book mode to read and gaming mode, and so on. The subject may select an on-screen keyboard mode or a quick phrase mode for communication, entertainment mode to listen music or watch movie, book mode to read and gaming mode. The on-screen keyboard may be controlled by one of the bodily-movements and/or physiological signals received from subject's brain.

Referring to a second screen 920 may be presented on the UI. The screen 920 may include a text box 922 placed on the top of the screen 920 where the typed texts are displayed. Further the screen 920 includes a predictive text entry box 924. The predictive text entry box 924 may include predictions that may appear during input of text in the screen 910. The character (letter) keys are arranged in alphabetical order considering the fact that disabled/aged people may not well accustomed with the QWERTY keyboards. Alternatively, the keyboard may be arranged in the QWERTY formats. The screen 920 is further shown to include options such as "Delete", "Speak", "Reset" and "Exit" on both right and left side of the screen 920 to minimize the time required to reach these keys depending on the current cursor position. For a key to be selected, the cursor needs to stay on that particular key for a minimum time. In an embodiment, said time can be changed by accessing 'settings' associated with the UI depending upon disabilities, needs, learning rate and cognitive abilities of the subject.

Figure 10:
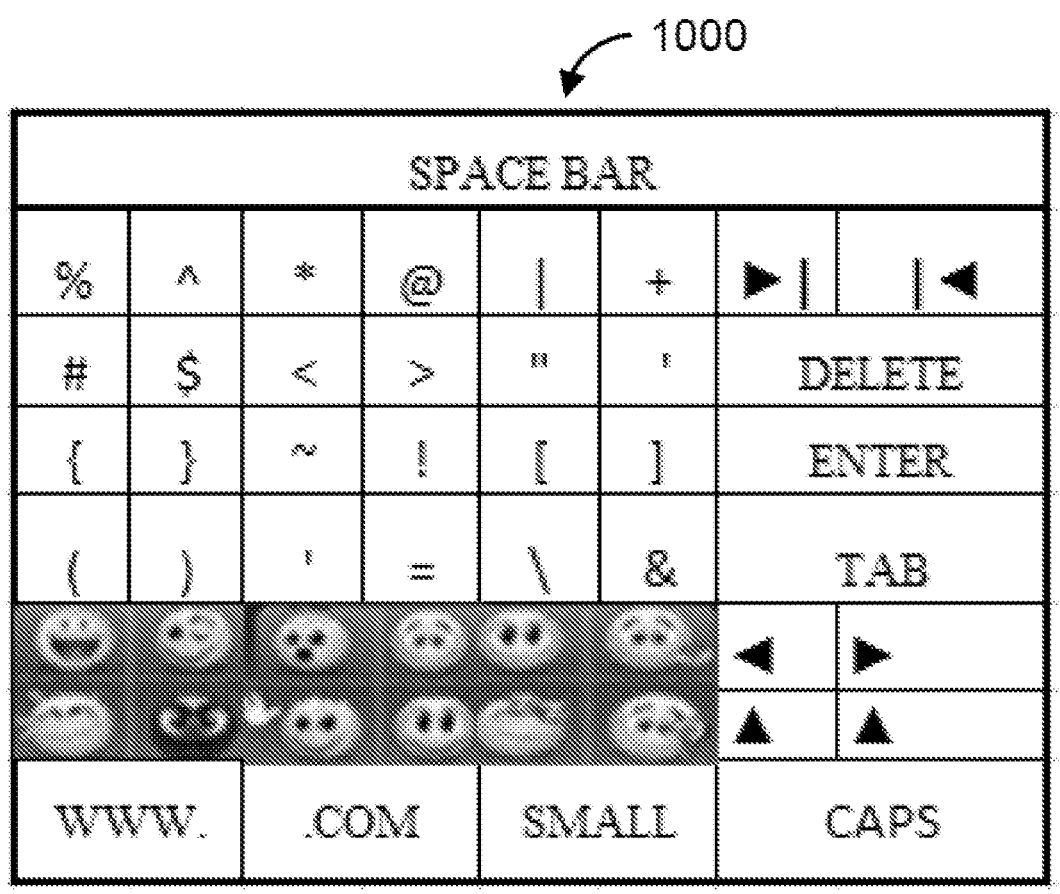
FIG. 10 illustrates a screenshot of an example UI for aiding communication, in accordance with another example embodiment.

FIG. 10 illustrates an example screenshots of an interactive UI 1000, in accordance with various embodiments of the present disclosure. In the present screen shot, the interactive UI 1000 presents various emoticons, and other non-alphabetical text for aiding the communication.

Various embodiments provide method and system for aiding communication for subjects suffering from paralysis of muscles controlled by peripheral nervous system. In such cases, the degradation of motion of body subject's parts happen progressively and eventually leading to complete termination of bodily motion. However, the eyeball movement, eye blinks, minute vibration of vocal track and certain facial muscles remain intact. The disclosed embodiments provide method and system to sense such bodily movements or movement intention by using various sensors and capture sensor data, and utilize said sensor data to enable communication with the subject. An important contribution of various embodiments is that the disclosed embodiment enables in designing a personalized system which adapts itself automatically to adjust to the changing state of the subject.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., are non-transitory. Examples include random access memory (RAM), read-only memory (ROM), volatile memory, non-volatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

The invention claimed is:

1. A processor-implemented method for aiding communication, the method comprising:
    capturing, from a plurality of sensors, sensor data generated based on an interaction of a subject with an interactive UI, via one or more hardware processors, the plurality of sensors comprising one or more body-parts movement tracking sensors for tracking motion of body-parts of the subject and one or more physiological signal sensors for monitoring physiological signals generated from the subject during the interaction;
    determining, based on the sensor data, a plurality of model parameters indicative of characteristics of the subject related to the interaction, via the one or more hardware processors, wherein the sensor data is collective sensor data from the one or more body-parts movement tracking sensors and the one or more physiological signal sensors, wherein the plurality of model parameters are determined by training a model, and wherein training the model comprises:
        monitoring dynamically, the sensor data generated based on the interaction of the subject with the interactive UI to determine a consistent change in the interaction, wherein determining the consistent change in the interaction comprises verifying, for a threshold number of times, change in the interaction of the subject with the interactive UI and a changed response of the subject due to progression of medical condition of the subject, to validate whether the changed response is consistent during the threshold number of times, and
        automatically updating, on determination of the consistent change, one or more model parameters from the plurality of model parameters based on the sensor data, and
    controlling navigation at the interactive UI based on the plurality of model parameters, via the one or more hardware processors.

2. The method as claimed in claim 1, wherein the one or more body-parts movement tracking sensors comprises Inertial Motion Unit (IMU), an electroencephalogram (EEG) sensor, eye tracking sensor, gyroscope, and magnetometer.

3. The method as claimed in claim 1, wherein the one or more physiological signal sensors comprises Galvanic Skin Response sensor and Photoplethysmogram sensor.

4. The method as claimed in claim 1, further comprising training the model for determining the plurality of model parameters, wherein training the model in an offline mode comprises:
    performing a plurality of known tasks and capturing a training sensor data during said performing, wherein the plurality of known tasks comprises interacting with the interactive UI; and
    obtaining a plurality of training model parameters based on the training sensor data, the plurality of training model parameters facilitates in training the model.

5. The method as claimed in claim 1, wherein controlling the navigation at the interactive UI comprises one or more of: indicating highlighting at least one element on the interactive UI, generating an audio output at the interactive UI and generating a visual output at the interactive UI.

6. The method as claimed in claim 1, further comprising adapting the interactive UI based on the updating of the one or more model parameters.

7. The method as claimed in claim 1, wherein the interactive UI comprises an on-screen keyboard layout.

8. The method as claimed in claim 1, further comprising storing the updated one or more model parameters at a server to derive an adapted interactive UI.

9. The method as claimed in claim 8, wherein adapting the interactive UI comprises adapting one or more elements of the interactive UI.

10. The method as claimed in claim 8, wherein adapting the interactive UI comprises adapting an orientation of a layout of the interactive UI.

11. A system for aiding communication, the system comprising:
    one or more memories storing instructions; and
    one or more hardware processors coupled to the one or more memories, wherein said one or more hardware processors are configured by said instructions to:
    capture, from a plurality of sensors, sensor data generated based on an interaction of a subject with an interactive UI, the plurality of sensors comprising one or more body-parts movement tracking sensors for tracking motion of body-parts of the subject and one or more physiological signal sensors for monitoring physiological signals generated from the subject during the interaction;
    determine, based on the sensor data, a plurality of model parameters indicative of characteristics of the subject related to the interaction, wherein the sensor data is collective sensor data from the one or more body-parts movement tracking sensors and the one or more physiological signal sensors, wherein the plurality of model parameters are determined by training a model, and wherein training the model comprises:

monitor dynamically, the sensor data generated based on the interaction of the subject with the interactive UI to determine a consistent change in the interaction, wherein determining the consistent change in the interaction comprises verifying, for a threshold number of times, change in the interaction of the subject with the interactive UI and a changed response of the subject due to progression of medical condition of the subject, to validate whether the changed response is consistent during the threshold number of times, and automatically update, on determination of the consistent change, one or more model parameters from the plurality of model parameters based on the sensor data, and control navigation at the interactive UI based on the plurality of model parameters.

12. The system as claimed in claim 11, wherein the one or more body-parts movement tracking sensors comprises Inertial Motion Unit (IMU), an electroencephalogram (EEG) sensor, eye tracking sensor, gyroscope, and magnetometer.

13. The system as claimed in claim 11, wherein the one or more physiological signal sensors comprises Galvanic Skin Response sensor and Photoplethysmogram sensor.

14. The system as claimed in claim 11, wherein the one or more hardware processors are further configured by the instructions to train the model for determining the plurality of model parameters, and wherein to train the model in an offline mode, the one or more hardware processors are further configured by the instructions to:

perform a plurality of known tasks and capturing a training sensor data during said performing, wherein the plurality of known tasks comprises interacting with the interactive UI; and obtain a plurality of training model parameters based on the training sensor data, the plurality of training model parameters facilitates in training the model.

15. The system as claimed in claim 11, wherein to control the navigation at the interactive UI, the one or more hardware processors are further configured by the instructions to perform one or more of: indicate highlighting at least one element on the interactive UI, generate an audio output at the interactive UI and generate a visual output at the interactive UI.

16. The system as claimed in claim 11, wherein the one or more hardware processors are further configured by the instructions to:

adapt the interactive UI based on the updating of the one or more model parameters; and store the updated one or more model parameters at a server to derive the adapted interactive UI.

17. The system as claimed in claim 16, wherein to adapt the interactive UI, the one or more hardware processors are further configured by the instructions to adapt one or more elements of the interactive UI.

18. The system as claimed in claim 16, wherein to adapt the interactive UI, the one or more hardware processors are further configured by the instructions to adapt an orientation of a layout of the interactive UI.

\* \* \* \* \*